US012644004B2

(12) United States Patent
Garbark

(10) Patent No.: US 12,644,004 B2
(45) Date of Patent: Jun. 2, 2026

(54) BIO-BASED COALESCING SOLVENTS

(71) Applicant: Battelle Memorial Institute, Columbus, OH (US)

(72) Inventor: Daniel B. Garbark, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 0 days.

(21) Appl. No.: 18/257,574

(22) PCT Filed: Dec. 14, 2021

(86) PCT No.: PCT/US2021/063390
§ 371 (c)(1),
(2) Date: Jun. 14, 2023

(87) PCT Pub. No.: WO2022/132820
PCT Pub. Date: Jun. 23, 2022

(65) Prior Publication Data

US 2024/0132728 A1 Apr. 25, 2024

Related U.S. Application Data

(60) Provisional application No. 63/125,265, filed on Dec. 14, 2020.

(51) Int. Cl.
*C09D 5/02* (2006.01)
*C07C 231/00* (2006.01)
(Continued)

(52) U.S. Cl.
CPC ................ *C09D 5/024* (2013.01); *C08K 5/06* (2013.01); *C08K 5/1535* (2013.01); *C09D 7/20* (2018.01);
(Continued)

(58) Field of Classification Search
CPC ... C07C 235/00; C07C 233/00; C07C 231/00; C09D 7/20; C08K 5/20
(Continued)

(56) References Cited

U.S. PATENT DOCUMENTS 8,653,180 B2 2/2014 Fu et al.
8,901,056 B2 12/2014 Griese et al.
(Continued)

FOREIGN PATENT DOCUMENTS

CN 1232053 A * 10/1999 .............. C08F 20/06
CN 1333298 A * 1/2002 ............ C08F 220/06
(Continued)

OTHER PUBLICATIONS

Machine translation of CN 1232053 (1999, 25 pages).*
(Continued)

*Primary Examiner* — Brieann R Johnston
(74) *Attorney, Agent, or Firm* — Susanne A. Wilson; Frank Rosenberg

(57) ABSTRACT

Coalescing solvents are among the most important components of water-borne latex paints and are required for deposition of continuous and tough films during the final stages of paint drying. Water-borne latex paints require 1-2 weight percent coalescing solvent which translates to use of about 770 million pounds in the US alone. This work focused on developing novel biobased coalescing solvents for water-borne latex paints to perform equivalent or better while being cost competitive to higher performing petroleum-based coalescing solvents. Formulation testing included minimum film forming temperature (MMFT), scrub resistance, freeze-thaw stability, and gloss. Other properties of the solvent considered were evaporation (leading to VOC content), density, viscosity, color, and hydrolytic stability. Hydrolytic stability is important for the shelf-life performance of the final paint formulation.

15 Claims, 1 Drawing Sheet

(51) Int. Cl.

| | |
|---|---|
| ***C07C 233/00*** | (2006.01) |
| ***C07C 235/00*** | (2006.01) |
| ***C08K 5/06*** | (2006.01) |
| ***C08K 5/1535*** | (2006.01) |
| ***C09D 7/20*** | (2018.01) |
| ***C09D 7/63*** | (2018.01) |

(52) U.S. Cl.
CPC .............. *C09D 7/63* (2018.01); *C07C 231/00* (2013.01); *C07C 233/00* (2013.01); *C07C 235/00* (2013.01)

(58) Field of Classification Search
USPC .................... 554/103, 108, 111, 112; 516/69
See application file for complete search history.

(56) References Cited

U.S. PATENT DOCUMENTS

| | | | |
|---|---|---|---|
| 10,533,108 | B2 | 1/2020 | Bene et al. |
| 2010/0240817 | A1 | 9/2010 | Joshi et al. |

FOREIGN PATENT DOCUMENTS

| | | | | |
|---|---|---|---|---|
| WO | 2008/054277 | A1 | | 5/2008 |
| WO | 2008/054277 | | * | 8/2008 |

OTHER PUBLICATIONS

McNutt (Development of biolubricants from vegetable oils via chemical modification, Journal of Industrial and Engineering Chemistry, 2016, 36, pp. 1-12).*
Turco (Synthesis of Biolubricant Basestocks from Epoxidized Soybean Oil, Catalysts, 2017, 7, 11 pages).*
Lee (Synthesis of Palm Oil-Based Diethanolamides, J Am Oil Chem Soc, 2007, 84, pp. 945-952).*
Machine translation of CN '298 (2002, 22 pages).*
International Preliminary Report on Patentability from International Application No. PCT/US2021/063390 dated Jun. 13, 2023.
Written Opinion of the International Search Authority from International Application No. PCT/US2021/063390 dated May 25, 2022.
International Search Report from International Application No. PCT/US2021/063390 dated May 25, 2022.

* cited by examiner

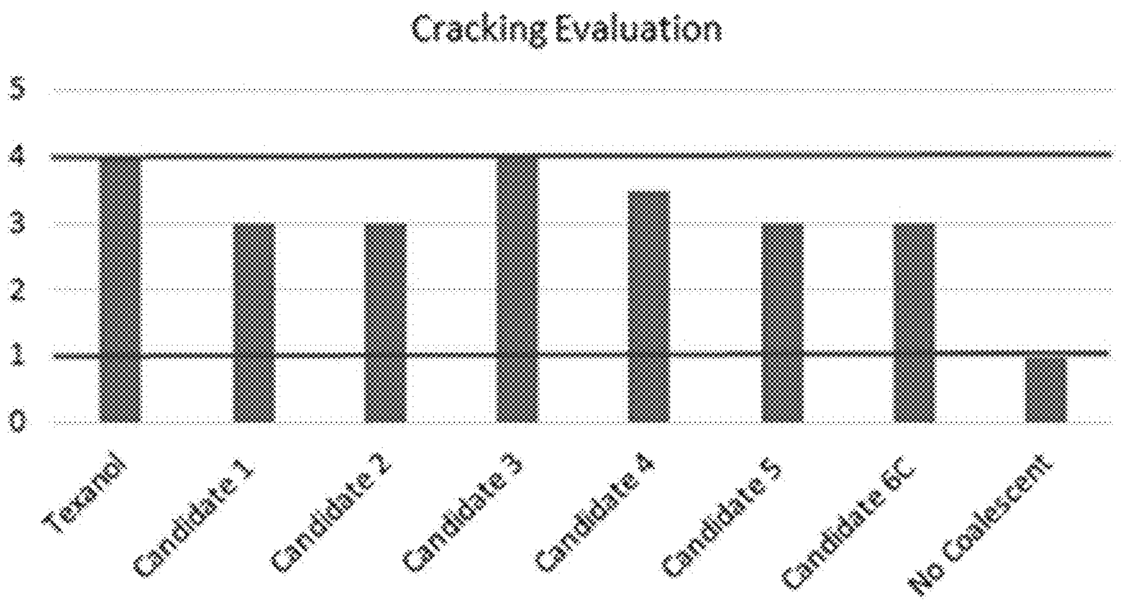
Fig. 1
Fig. 2

BIO-BASED COALESCING SOLVENTS

RELATED APPLICATIONS

This application is a national stage filing and claims the priority benefit of PCT/US2021/063390, filed 14 Dec. 2021, and claims the priority benefit of U.S. Provisional Patent Application Ser. 63/125,265 filed 14 Dec. 2020.

SUMMARY OF THE INVENTION

The invention includes any of the compounds described or drawn herein. The invention includes paints (generally including water-borne coatings) and paint precursor compositions. The invention also includes methods of coating a surface using any of the compositions described herein.

In a first aspect, the invention provides a coating composition, comprising water, a polymer, and one or more compounds selected from candidates 1-12. For example, the coating composition comprises:

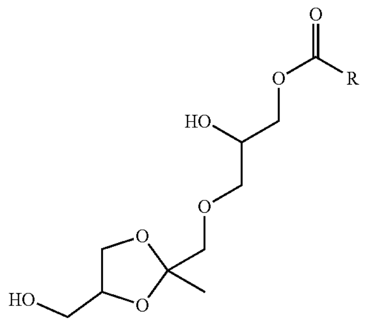

where R comprises a chain of one to twenty-four carbons. The chain can be olefinic, alkyl, or branched alkyl. In some preferred embodiments, the ester group is either isobutyric or soy fatty acid. The fatty acid moiety may also comprise an epoxide, hydroxyl, or ether group. Other candidates can be based on derivatives of high oleic fatty acid epoxides where the epoxide has been ring opened with a compatibility enhancer. These enhancers could materials such as, but not limited to, propylene glycol, dipropylene glycol, tripropylene glycol, diethylene glycol, triethylene glycol, 2-ethoxyethanol, diethylene glycol mono-methyl ether, diethylene glycol mono-ethyl ether, dipropylene glycol mono-methyl ether, 1-methoxy-2-propanol, or any alkoxylated polyol including mono-ethers thereof. In another example, the coating composition comprises:

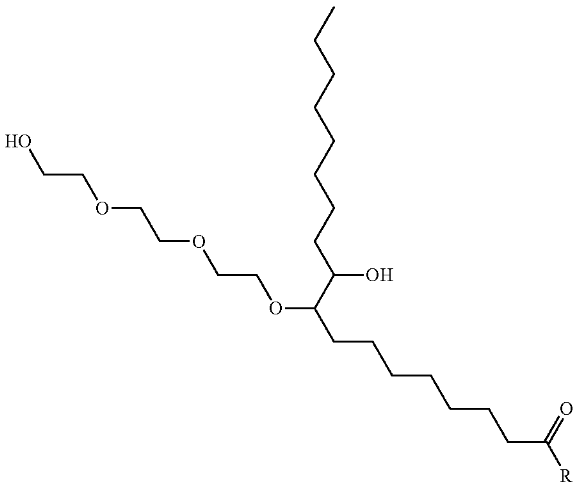

wherein R is a moiety OR' wherein R' comprises a C1-C24 alkyl that can be olefinic, alkyl, or branched alkyl; or wherein R is a moiety $NR^1R^2$ wherein $R^1$ comprises a C1-C24 alkyl that can be olefinic, alkyl, or branched alkyl; and $R^2$ comprises a C1-C24 alkyl that can be olefinic, alkyl, or branched alkyl; the alkyl may further comprise a functional group such as an OH moiety.

The invention can be further characterized by one or any combination of the following: comprising at least 0.5 wt % (or at least 1, at least 2, or at least 5 wt %) of one or more compounds selected from candidates A-J; wherein the one or more compounds is at least 50% biobased carbon, or at least 70% biobased carbon; wherein the composition comprises 0.5 to 5 wt % (or 0.5 to 3.0 wt %, or 1 to 2 wt %) of one or any combination of the candidates 1-12; wherein the composition comprises one or more of a pigment, hydroxy ethyl cellulose, defoamer, propylene glycol, and a surfactant.

The invention also provides a method of coating a substrate comprising applying any of the compositions described herein, and allowing water to evaporate to produce a coating on the surface. Preferably, the coating exhibits no cracking or only slight cracking that is only visible by magnification.

In another aspect, the invention comprises a coated substrate comprising the substrate and a coating comprising any of candidates 1-12. The invention also includes a coated substrate made by coating a substrate with any of the compositions described herein. A coated substrate is schematically illustrated in cross-section in FIG. 2 with the coating layer on top of the substrate.

In a further aspect, the invention comprises a method of making a coalescing agent, comprising: providing an oil comprising at least 50% wt % or at least 70 wt % or 70 to 99 wt % oleic acid or other oleate; reacting the oleic acid or other oleate to form an epoxide; reacting the epoxide with propylene glycol, dipropylene glycol, tripropylene glycol, diethylene glycol, triethylene glycol, 2-ethoxyethanol, diethylene glycol mono-methyl ether, diethylene glycol mono-ethyl ether, dipropylene glycol mono-methyl ether, 1-methoxy-2-propanol, or any alkoxylated polyol. Furthermore, the invention comprises combining the resulting coalescing agent with a one or more paint components to form a paint. The invention also includes a paint comprising any of the coalescing agents made by the methods described here.

Any aspect of the invention may also be described in conjunction with one or any combination of the test results reported herein, or ±10%, or ±20%, or ±30% of one or any combination of the test results reported herein. For example, no loss of gloss or ±10%, or ±20%, or ±30% change in gloss after 1, 2, or 3 freeze-thaw cycles at any of the listed temperatures. The compounds and intermediates herein preferably contain a carbon content that is at least 50% or 100% biobased. The compounds and intermediates are preferably derived from soybeans. Note that bio-based compositions can be identified by knowledge of their derivation or $^{14}C$ levels as is known in the literature. Any of the compounds can be further characterized by one or any combination of the results described herein (or within ±10%, or ±20%, or ±30% of the results described herein). The superior results observed for the compounds was a surprising result, especially for bio-based coalescing agents.

BRIEF DESCRIPTION OF THE DRAWINGS

FIG. 1 shows testing results of the extent of cracking.

FIG. 2 schematically illustrates a coated substrate in cross-section with the coating layer on top of the substrate.

DETAILED DESCRIPTION OF THE INVENTION

Coalescing solvents are latex paint additives that help the polymeric coating evenly disperse leading to smooth and tough paint coatings. The main performance characteristics of a good solvent in latex paint is low minimum film forming temperature, high scrub resistance of the cured paint, minimal changes in viscosity and homogeneity of the mixture from freeze-thaw cycles, and high gloss measurements in the cured paint. Another important trait of coalescing solvents is hydrolytic stability. Paints are typically slightly basic in aqueous systems. The basicity is due to additives such as fillers and pigments that are present in the paint formulations. This means that some ester solvents will rapidly degrade by hydrolysis during storage. Hydrolysis can be mitigated by either removing the ester functional group or, as in the case of one of our candidates, create branching that hinders hydrolysis of esters. For this reason and others, solvent properties must be carefully considered.

Battelle has developed synthetic pathways from soy components. The process for inter- and intra-molecular reactions can be seen below.

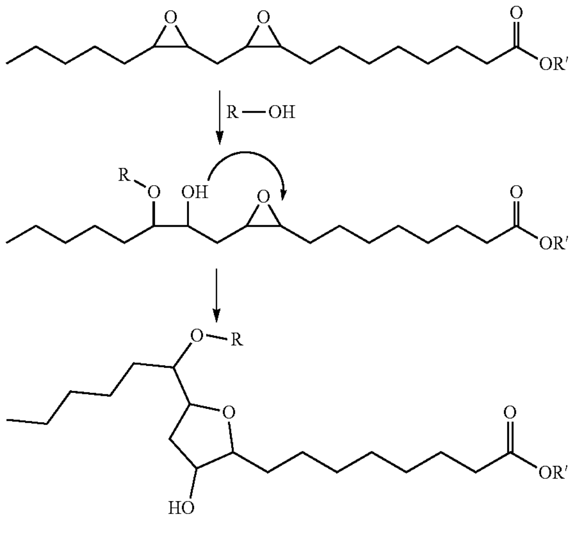

In this work, new coalescing solvents were then produced for evaluation in standard latex paint formulations. The initial candidates were compiled and evaluated at a standard test house for minimum film forming temperature, scrub resistance, freeze-thaw stability, and gloss. The initial candidates conceived for this work can be found in the table below.

| Candidate | Description |
|---|---|
| 1 | Glycerol Monopropyl Ether + Isobutyric Acid |
| 2 | Glycerol Monopropyl Ether |
| 3 | Isoprene + Glycerol |
| 4 | Chelator Intermediate (Glycerol + Acrylonitrile) |
| 5 | 2-Butyl Epoxidized High Oleic Soybean Oil + Isobutyric Acid |
| 6A | Propylamine + Epoxidized Methyl High Oleic Soybean Oil + Ethanol |
| 6B | Ethanolamine + Epoxidized Methyl High Oleic Soybean Oil + Ethanol |
| 6C | Diethanolamine + Epoxidized Methyl High Oleic Soybean Oil + Ethanol |
| 7 | Regular Soybean Oil Version of 6 (Not attempted due to iterations of 6) |
| 10 | Glycerol Ketone-Ether |

Solvents were prescreened by looking at cracking of coatings on paper. A thin film was spread and allowed to dry on paper. Once dry, the paper was bent and evaluated for cracking in the coating. The standard formulation and process for compilation can be found below. The cracking results are shown in FIG. 1. In FIG. 1, the numerical scale is as follows: 0=film chips off completely; 1=severe cracking; 2=moderate cracking; 3=some cracking, just visible to the eye; 4=slight cracking, only visible by magnification; 5=no cracking.

| Materials | Pounds/ Gallon | Grams/ Gallon | Order of addition |
|---|---|---|---|
| Water | 3.75 | 1702.24 | 1 |
| Hydroxy Ethyl Cellulose $_1$ | 0.03 | 11.35 | 7 |
| Kathon ® LX 1.5% $_2$ | 0.02 | 10.21 | 2 |
| Tamol ® 731 (25%) $_2$ | 0.08 | 34.04 | 3 |
| KTPP (100%) $_3$ | 0.01 | 5.67 | 8 |
| Defoamer4 | 0.03 | 11.35 | 4 |
| Tergital NP-9 | 0.03 | 22.70 | 5 |
| Propylene Glycol | 0.56 | 255.34 | 6 |
| Titanium Dioxide $_6$ | 2.50 | 1134.83 | 11 |
| Calcined Clay $_7$ | 0.94 | 425.56 | 10 |
| Calcium Carbonate $_8$ | 0.94 | 425.56 | 9 |
| | Letdown | | |
| Rovace ™ 9100 (55%) $_2$ | 2.94 | 1333.62 | 12 |
| Coalescent | 0.13 | 58.99 | |
| Defoamer $_4$ | 0.02 | 9.08 | 13 |
| Water | 0.57 | 258.19 | 14 |
| Acrysol ® RM-825 (25%) $_2$ | 0.19 | 86.22 | 15 |
| Aqueous Ammonia (28%) | 0.01 | 4.54 | 16 |
| Total | 10.98 | 4,980.53 | |

All materials added per addition order into 1 gallon roller mill jar, while stirring with mixer after addition of item 11 mix for additional 5 min then add grinding media to roller jar place on roller mill for 24-48 hours hegman reading after 28 hrs 7.5

After 28 hrs remove top on roller mill jar and place cheese cloth over top to remove paint into a 2 gallon bucket keeping the grinding media in jar, then rinse roller mill jar & grinding media with hot water until cleaned.

Once paint is in 2 gallon bucket add remaining ingredients in order of addition, allow to mix for 10-15 min after all items in.

Cap bucket until ready to transfer to quart cans.

While mixing the paint in quart cans add the experimental bio-based coalescent solvents at 1.18% based on total weight.

Each quart with a different bio-based coalescent solvent

Candidates 3 and 4 performed similarly to the control petroleum standard Texanol. This provided guidance for the candidate focus on further testing. Candidates were formulated and tested as stated above and sent for testing.

| Coalescing Solvent Data Description | MFFT ° C. at 2.9% | Scrub Resistance % Standard | Freeze-Thaw Stability Ratings-After 3 Cycles | | | | | | Initial Gloss-after 3 Freeze Thaw Cycles 85° | Final Gloss-after 3 Freeze Thaw Cycles 85° |
|---|---|---|---|---|---|---|---|---|---|---|
| | | | Separation | Gelation | Coagulation | Initial Stormer | Final Stormer | Temp ° C. | | |
| Standard | 4.3 | 304 | Very Slight | None | None | 99 | 129 | 25 | 9.0 | 4.3 |
| Candidate 3 | 2.8 | 298 | Slight | None | None | 113 | 108 | 25 | 7.8 | 7.6 |
| Candidate 4 | 3.3 | 280 | Moderate | None | None | 101 | 97 | 25 | 7.6 | 7.1 |
| Candidate 6c | 7.3 | 113 | Slight | None | None | 101 | 98 | 25 | 10.2 | 9.7 |
| Candidate 8 | 2.9 | 266 | Slight | None | None | 97 | 101 | 25 | 8.7 | 7.6 |
| Candidate 3a | 5.4 | 276 | Very Slight | None | None | 92.3 | 93.8 | 25 | 7.6 | 7.1 |
| Candidate 10 | 5.3 | 287 | Very Slight | None | None | 91.0 | 91.1 | 25 | 6.6 | 6.4 |

% Solids between 48.5-49.5%

All made with standard formulation using Rovace® 9100. Testing can be conducted using ASTM-D2243.

The results showed that the soy-based solvents don't suffer changes in viscosity and gloss after three Freeze-Thaw cycles. Surprisingly, scrub resistance and minimum film formation temperatures for the bio-based coalescence agents are comparable to the industrial standard Texanol. Candidate structures are found below along with others expected to improve performance further.

Candidate 1

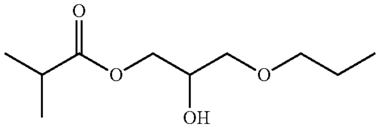

Candidate 2

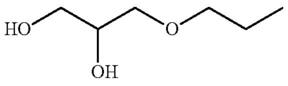

Candidate 3

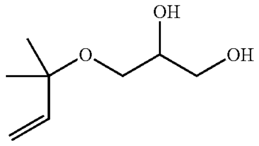

Candidate 4

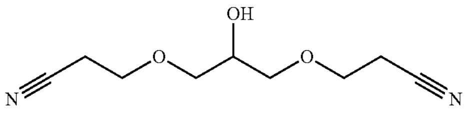

Candidate 5

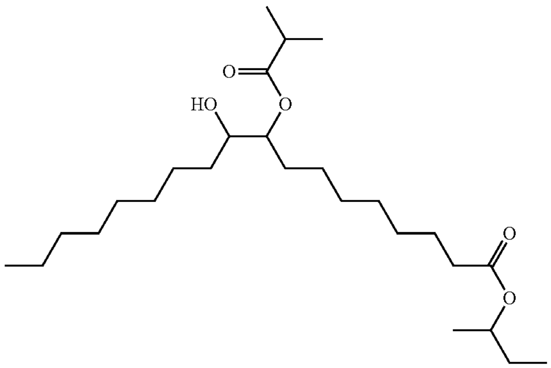

-continued

Candidate 6c

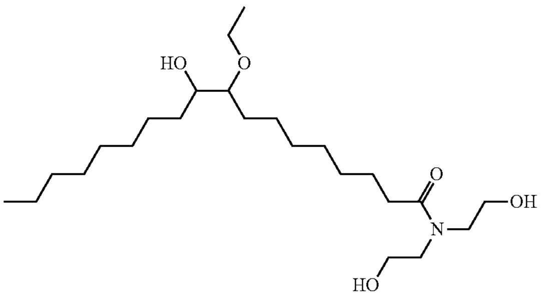

Candidate 7

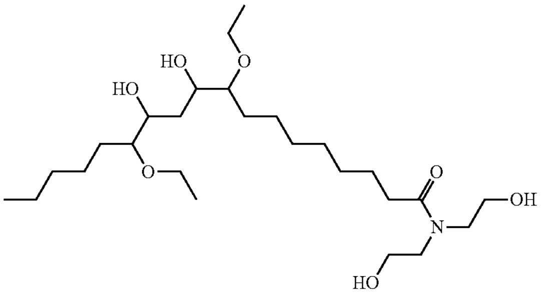

Candidate 10

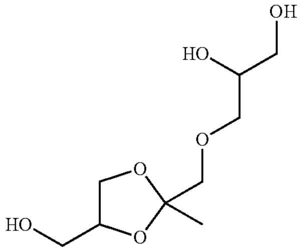

Candidate 11

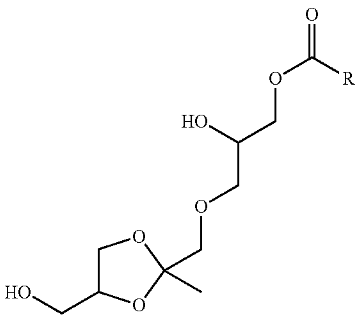

Where R is C1-C24 and can be olefinic, alkyl, or branched alkyl. In some preferred embodiments, the ester group is either isobutyric or soy fatty acid. The fatty acid moiety may also comprise an epoxide, hydroxyl, or ether group.

As used in this specification, "alkyl" includes species comprising one or more of a saturated straight chain or branched alkyl groups having from 1 to 24 carbon atoms. Representative saturated straight chain alkyls include -methyl, -ethyl, -n-propyl, -n-butyl, -n-pentyl, -n-hexyl, -n-heptyl, -n-octyl, -n-nonyl, -n-decyl and the like. Representative branched alkyls include, but are not limited to, -isopropyl, -sec-butyl, -isobutyl, -tert-butyl, -isopentyl, -2-methylbutyl, -3-methylbutyl, -2,2-dimethylbutyl, -2,3-dimethylbutyl, -2-methylpentyl, -3-methylpentyl, -4-methylpentyl, -2-methylhexyl, -3-methylhexyl, -4-methylhexyl, -5-methylhexyl, -2,3-dimethylbutyl, -2,3-dimethylpentyl, -2,4-dimethylpentyl, -2,3-dimethyleyl, -2,4-dimethylhexyl, -2,5-dimethyleyl, -2,2-dimethylpentyl, -2,2-dimethylhexyl, -3,3-dimethylpentyl, -3,3-dimethylhexyl, -4,4-dimethylhexyl, -2-ethylpentyl, -3-ethylpentyl, -2-ethylhexyl, -3-ethylhexyl, -4-ethylhexyl, -2-methyl 2-ethylpentyl, -2-methyl-3-ethylpentyl, -2-methyl-4-ethylpentyl, -2-methyl 2-ethylhexyl, -2-methyl-3-ethylhexyl, -2-methyl-4-ethylhexyl, -2,2-diethylpentyl, -3,3-dethylhexyl, -2,2-dethylhexyl, and -3,3-dethylhexyl.

Other candidates can be based on derivatives of high oleic fatty acid epoxides where the epoxide of the precursor has been ring opened with a compatibility enhancer. These enhancers could materials such as, but not limited to, propylene glycol, dipropylene glycol, tripropylene glycol, diethylene glycol, triethylene glycol, 2-ethoxyethanol, diethylene glycol mono-methyl ether, diethylene glycol mono-ethyl ether, dipropylene glycol mono-methyl ether, 1-methoxy-2-propanol, or any alkoxylated polyol including mono-ethers thereof. A candidate is shown below:

Candidate 12

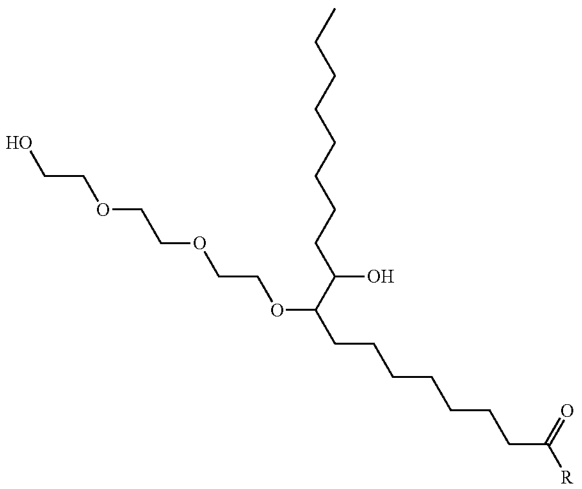

R may be derived from any alcohol (ROH) to form an ester (—C(O)R' wherein R' is —OR) group (preferably a branched alcohol to give hydrolytic stability), polyol, amide, or amide alcohol. Preferably R comprises a C1-C24 moiety that can be olefinic, alkyl, or branched alkyl. The structure will give good hydrolytic stability in paint formulations allowing for long term shelf storage once formulated.

Other Components

In addition to the coalescing agents, a composition may comprise components such as pigments, surfactants, defoamers, thickeners, co-solvents (such as propylene glycol or ethylene glycol), corrosion inhibitors, and wetting agents.

Aqueous latex paints are used for both architectural and industrial use, indoors and outdoors, the invention applies not only to such paints, but also to other aqueous dispersions referred to as water-borne coatings. These paints and coatings, along with a coalescing solvent typically include one or more water-dispersible polymers, one or more low number average molecular weight polymers (such as polyethylene glycol or polypropylene glycol) preferably having a number average molecular weight of about 300 to about 20,000 Daltons, and may comprise one or more rheology modifiers, for instance a thickener.

As is known, latex paints comprise polymers. Polymers comprise repeating units. A "copolymer" is a polymer comprising at least two different component units, each of which units corresponds to (and is derived from) a different monomer. Thus, a copolymer comprising component units corresponding to three different monomers (also known as a terpolymer) is included within the term "polymer," as is a polymer comprising one component unit (also known as a homopolymer). Acrylate polymers can be, for example, 10% to 50% (or 20 to 40%) by weight of the aqueous composition. Polymers in the latex can be, for example, polyacrylate, styrenic monomers such as styrene-acrylic, or styrene-butadiene, vinyl-based polymers such as poly-vinyl acrylate, or vinyl-acrylic.

The composition may comprise water-soluble polymers, including but not limited to polycarboxylic acids, copolymers comprising monomers containing a carboxylic acid, water soluble copolymers, cellulose derivatives, salts of polyacrylic acids, salts of copolymers comprising monomers containing an acrylic acid, polyvinylpyrrolidone, and copolymers comprising vinylpyrrolidone monomer. In another embodiment, the water-soluble polymer is a salt of a polyacrylic acid, a salt of a copolymer comprising a monomer containing an acrylic acid, or a mixture thereof.

Conventional emulsifiers or surfactants, i.e., anionic, cationic, nonionic, amphoteric surfactants and mixtures thereof, can also be used in compositions of the invention. The amount of one or more surfactant is preferably from about 0.01% to about 10% by weight, more preferably be from about 0.1% to about 5% by weight, and especially preferably about 0.2% to about 3% by weight. Commonly utilized nonionic emulsifiers are alkylphenol ethoxylates and derivatives thereof, such as nonylphenol ethoxylate. Emulsifiers may include tri-styryl phenol ethoxylates.

Anionic emulsifiers include but are not limited to alkali metal alkyl aryl sulfonates, alkali metal alkyl sulfates, the sulfonated alkyl esters, e.g., sodium dodecylbenzene sulfonate, sodium disecondary-butylnaphthalene sulfonate, sodium lauryl sulfate, disodium dodecyldiphenyl ether disulfonate, disodium n-octadecylsulfosuccinamate, sodium dioctylsulfosuccinate, and the like. Cationic emulsifiers include but are not limited to amines, e.g., aliphatic mono-, di- and polyamines derived from fatty and rosin acids; and quaternary ammonium salts, e.g., dialkyldimethyl and alkyltrimethyl ammonium salts, alkylbenzyldimethyl ammonium chlorides, and alkylpyridinium halides.

Amphoteric emulsifiers include but are not limited to imidazoline derivatives, such as disodium lauroampho diacetate, disodium cocoampho diacetate, sodium cocoampho acetate, sodium cocoampho propionate, sodium lauroampho acetate, disodium cocoampho dipropionate, cocoampho dipropionic acid, sodium capryloampho carboxylate, sodium cocoampho hydroxypropyl sulfonate, sodium capryloampho hydroxypropyl sulfonate, and the like; alkyl betaines, such as lauramidopropyl betaines, coco dimethyl betaine, oleamidopropyl betaine, and the like; sultaines, such as alkylether hydroxypropyl sultaine, cocamidopropyl hydroxyl sultaine, and the like; dihydroxyethyl glycinates, such as dihydroxyethyl tallow glycinate and the like; and aminopropionates, such as sodium laurimino dipropionate and the like. The foregoing emulsifiers can be separately or as a mixture of two or more thereof.

A copolymer surfactant typically has a number average molecular weight of from about 300 Daltons to about 400,000 Daltons, or from about 400 to about 200,000 Daltons, or from about 1,200 to about 200,000 Daltons.

Exemplary optional thickeners include nonionic hydrophobically modified ethylene oxide urethane block copolymers, hydrophobically-modified polyethers, hydrophobically-modified alkali soluble emulsions, hydrophobically-modified poly(meth)acrylic acid, hydrophobically-modified hydroxyethyl cellulose, hydrophobically-modified poly (acrylamide), and mixtures thereof.

Pigments may comprise one or more natural or synthetic pigments or natural or synthetic dyes or combinations thereof, for example titanium dioxide, zinc oxide, calcium carbonate, aluminum oxide, aluminum silicate, silica, talc, and clay. Such pigments are well-known in the art. Organic pigments include phthalocyanine blue, phthalocyanine green, monoarylide yellow, diarylide yellow, benzimidazolone yellow, heterocyclic yellow, DAN orange, quinacridone magenta, quinacridone violet, organic reds, including metallized azo reds and nonmetallized azo reds, and the like. Exemplary azo reds include lithols, lithol rubine, toluidine red, naphthol red and quinacridone red. Metallized azo reds are salts containing metal cations, such as barium or calcium salts of azo reds, e.g., calcium lithol rubine and barium lithol red. Inorganic pigments include carbon black, lampblack, black iron oxide, yellow iron oxide, brown iron oxide, red iron oxide, and the like.

What is claimed is:

1. A paint composition, comprising water, a polymer, and

Candidate 6c

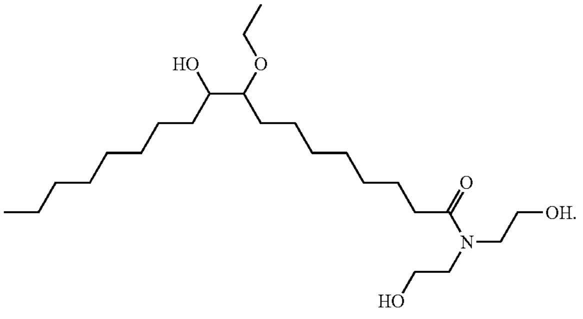

2. The paint composition of claim 1 comprising at least 0.5 wt %:

Candidate 6c

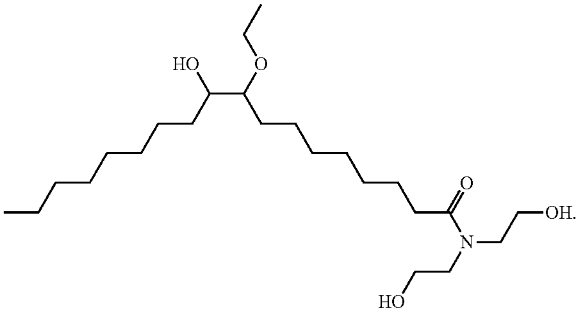

3. The composition of claim 2 wherein the Candidate 6c is at least 50% biobased carbon.

4. The paint composition of claim 1 wherein the composition comprises 0.5 to 5 wt % of:

Candidate 6c

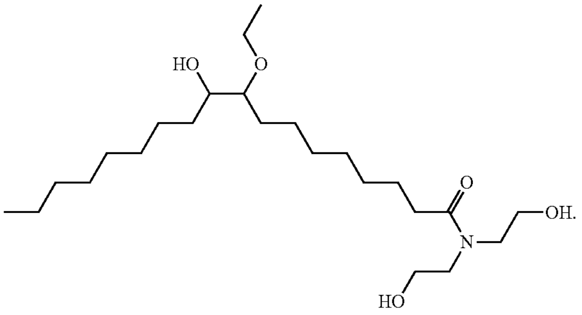

5. The paint composition of claim 4 further comprising a pigment, hydroxy ethyl cellulose, defoamer, propylene glycol, and a surfactant.

6. A method of coating a substrate comprising applying the paint composition of claim 1 to a surface, and allowing water to evaporate to produce a coating on the surface.

7. A coated substrate comprising a substrate and a paint comprising:

Candidate 6c

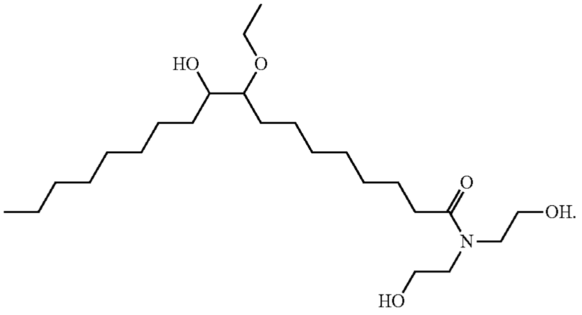

8. The method of claim 6 wherein the coating exhibits no cracking or only slight cracking that is only visible by magnification.

9. The coated substrate of claim 7 wherein the coating has stability such that viscosity and/or gloss changes by 10% or less after three Freeze-Thaw cycles.

10. The coated substrate of claim 7 wherein the coating exhibits a 30% or less change in gloss after three Freeze-Thaw cycles to 85° C.

11. The paint composition of claim 1 comprising at least 2 wt % of:

Candidate 6c

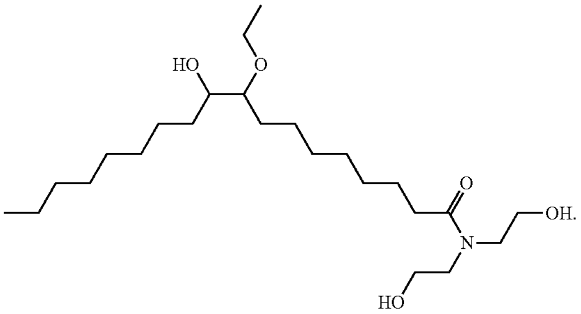

12. The paint composition of claim 1 comprising at least 5 wt % of:

Candidate 6c

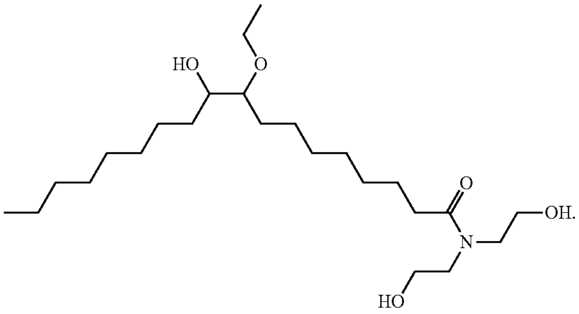

13. The composition of claim 2 wherein the Candidate 6c is at least 70% biobased carbon.

14. The coated substrate of claim 7 wherein the coating exhibits a 20% or less change in gloss after three Freeze-Thaw cycles to 85° C.

15. The coated substrate of claim 7 wherein the coating exhibits a 10% or less change in gloss after three Freeze-Thaw cycles to 85° C.

* * * * *